(12) United States Patent
Hall et al.

(10) Patent No.: US 7,795,023 B2
(45) Date of Patent: Sep. 14, 2010

(54) IDENTIFICATION OF A PLURIPOTENT PRE-MESENCHYMAL, PRE-HEMATOPOIETIC PROGENITOR CELL

(75) Inventors: Frederick L. Hall, Glendale, CA (US); Erlinda M. Gordon, Glendale, CA (US)

(73) Assignee: The University of Southern California, Los Angeles, CA (US)

( * ) Notice: Subject to any disclaimer, the term of this patent is extended or adjusted under 35 U.S.C. 154(b) by 1224 days.

(21) Appl. No.: 10/404,714

(22) Filed: Mar. 31, 2003

(65) Prior Publication Data

US 2003/0157078 A1    Aug. 21, 2003

Related U.S. Application Data

(62) Division of application No. 09/619,865, filed on Jul. 20, 2000, now abandoned.

(60) Provisional application No. 60/144,786, filed on Jul. 20, 1999.

(51) Int. Cl.
*C12N 5/00* (2006.01)
*C12N 5/07* (2006.01)
*C12Q 1/68* (2006.01)
*G01N 33/53* (2006.01)

(52) U.S. Cl. .................. 435/375; 435/377; 435/397; 435/6; 435/7.1

(58) Field of Classification Search ............ 435/375, 435/377, 397
See application file for complete search history.

(56) References Cited

U.S. PATENT DOCUMENTS

| | | | |
|---|---|---|---|
| 5,166,065 A | 11/1992 | Williams et al. | |
| 5,226,914 A | 7/1993 | Caplan et al. | |
| 5,486,359 A | 1/1996 | Caplan et al. | |
| 5,670,372 A | 9/1997 | Hogan | |
| 5,766,950 A * | 6/1998 | Greenberger et al. | 435/397 |
| 5,776,193 A | 7/1998 | Kwan et al. | |
| 5,849,287 A | 12/1998 | Greenberger et al. | |
| 6,004,798 A | 12/1999 | Anderson et al. | |
| 6,358,737 B1 | 3/2002 | Bonewald et al. | |
| 6,361,997 B1 | 3/2002 | Huss | |
| 6,518,063 B1 * | 2/2003 | Ducy et al. | 435/325 |

FOREIGN PATENT DOCUMENTS

| | | |
|---|---|---|
| JP | 11-18787 A | 1/1999 |
| JP | 2003-527817 A | 9/2003 |
| WO | WO9820907 | 5/1998 |
| WO | WO 00/06705 | 2/2000 |

OTHER PUBLICATIONS

Centrella M, McCarthy TL, Canalis E. Transforming growth factor beta is a bifunctional regulator of replication and collagen synthesis in osteoblast-enriched cell cultures from fetal rat bone. J Biol Chem. 1987;262(6):2869-74.*

Pittenger MF, Mackay AM, Beck SC, Jaiswal RK, Douglas R, Mosca JD, Moorman MA, Simonetti DW, Craig S, Marshak DR. Multilineage potential of adult human mesenchymal stem cells. Science. 1999; 284(5411):143-147.*

Prockop DJ. Marrow stromal cells as stem cells for nonhematopoietic tissues. Science. 1997; 276(5309):71-74.*

Chen et al The Journal of Cell Biology, 1998, vol. 142 (1), 295-305.*

Buehr et al, Philos Trans R Soc Lond B Biol Sci. 2003; 358(1436): 1397-402.*

Gorba et al Pharmacol Res, 47(4): 2003, 269-78.*

Mizuno et al Biochem Biophy. Commun. Res. 1995, 211, (3), 1091-1098.*

Kucia et al Leukemia. 2005; 19(7):1118-27.*

Pera et al Journal of Cell Science, 2000, 113, 5-10.*

Ducy et al Curr Opin Cell Biol. Oct. 1998;10(5):614-9.*

Hall, et all, "Phenotypic Differentiation of TGF-β1-Responsive Pluripotent Premesenchymal Prehematopoietic Progenitor (P4 Stem) Cells from Murine Bone Marrow", *Journal of Hematotherapy & Stem Cell Research*, vol. 10, pp. 261-271, 2001.

Gordon, et al., "Capture and Expansion of Bone Marrow-Deprived Mesenchymal Progenitor Cells with a Transforming Growth Factor-β1-von Willebrand's Factor Fusion Protein for Retrovirus-Mediated Delivery of Coagulation Factor IX", *Human Gene Therapy*, vol. 8, pp. 1385-1394, Jul. 20, 1997.

Ducy, et al., "Osf2/Cbfal: A Transcriptional Activator of Osteoblast Differentiation" *Cell*, vol. 89, pp. 747-754, May 30, 1997.

Fraichard et al., "In vitro differentiation of embryonic stem cells into glial cells and functional neurons," 1995, *Journal of Cell Science*, 108:3181-3188.

Horwitz et al., "Transplantability and therapeutic effects of bone marrow-derived mesenchymal cells in children with osteogenesis imperfecta," 1999, *Nature Medicine*, vol. 5, pp. 309-313.

Prockop, "Marrow Stromal Cells as Stem for Nonhematopoietic Tissues," 1997, *Science*, vol. 276, pp. 71-74.

Koc, On, et al., "Mesenchymal Stem Cells: Heading into the Clinic," *Bone Marrow Transplantation*, vol. 27, pp. 235-239, 2001.

Gordon, E.M., "Capture & Expression of Bone Marrow-Derived Mesenchymal Progenitor Cells with a transforming Growth Factor-B1von Willebrand's factor fusion protein for retrovirus-mediated delivery of coagulation Factor IX," 9*Hum. Gen. Ther.*, 8:1385-1394, 1997.

(Continued)

*Primary Examiner*—Deborah Crouch
*Assistant Examiner*—Anoop Singh
(74) *Attorney, Agent, or Firm*—Wilson Sonsini; Goodrich & Rosati

(57) ABSTRACT

The present invention provides a molecular marker for the identification of pluripotent pre-mesenchymal, pre-hematopoietic stem cells. The invention further provides primitive progenitor cells identified by the molecular marker. Such cells have the potential to differentiate into both mesenchymal and hematopoietic phenotypes, as determined by a proliferative response to inductive growth factors and cytokines, and by their morphologic and cytochemical features.

8 Claims, 7 Drawing Sheets

OTHER PUBLICATIONS

Hanada, et al., "Stimulatory Effects of Basic Fibroblast Growth Factor and Bone Morphogenetic Protein-2 on Osteogenic Differentiation of Rat Bone Marrow-Derived Mesenchymal Stem Cells", *Journal of Bone and Mineral Research*, vol. 12, No. 10, pp. 1606-1614, 1997.

Jikken Igaku, "Molecular Mechanisms of Bone Formation" *Experimental Medicine* 16(11):1343-1350 (1998).

Canadian IPO; Requisition by the Examiner in Application No. 2,379,683; Feb. 7, 2008.

* cited by examiner

FIG. 3A
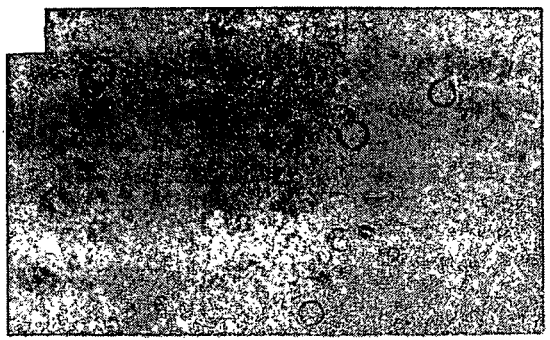
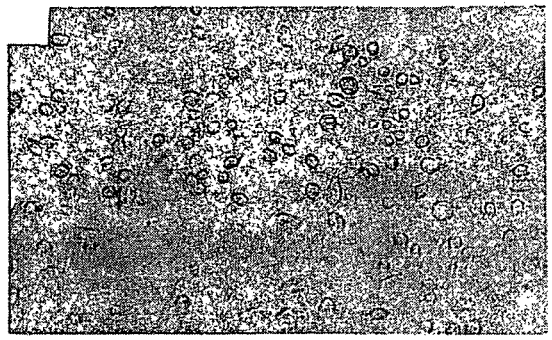
PRE-MESENCHYMAL STEM CELLS
FIG. 3B
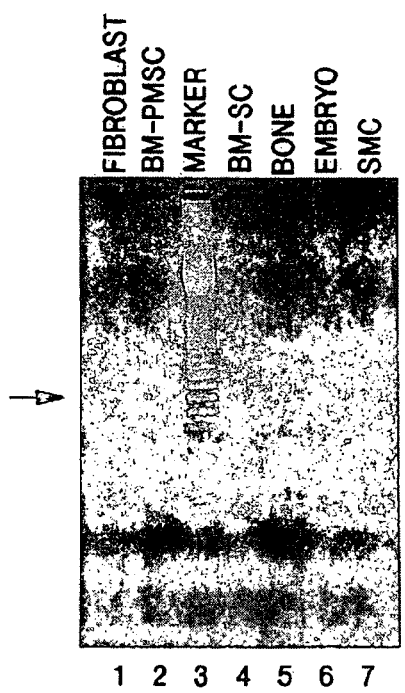
FIG. 3C

IDENTIFICATION OF A PLURIPOTENT PRE-MESENCHYMAL, PRE-HEMATOPOIETIC PROGENITOR CELL

CROSS REFERENCE TO RELATED APPLICATIONS

This application is a Divisional of U.S. patent application Ser. No. 09/619,865, filed Jul. 20, 2000 now abandoned, which claims priority to U.S. Provisional Application Serial No. 60/144,786, filed Jul. 20, 1999, the disclosures of which are incorporated herein by reference.

TECHNICAL FIELD

This invention relates generally to the isolation and identification of cytokine-responsive stem cells and more particularly to pluripotent pre-mesenchymal, pre-hematopoietic progenitor cells expressing a unique molecular marker and a method for identifying such cells.

BACKGROUND

Primitive progenitor cells from bone marrow are useful targets for cell-based therapies due to their self-renewing potential, multilineage differentiation, and demonstrable contribution to somatic tissues (Fellari et al., Science, 279: 1528, 1998). Prevailing dogma defines three histogenetically distinct cellular systems in the bone marrow: hematopoietic cells, endothelial cells, and stromal cells, yet subsumes no common precursors in post-natal mammals (Waller et al., Blood, 85:242, 1995). Hematopoietic stem cells have been widely studied, and their lineage diagram and differentiation pathways have been defined by a number of cell surface markers as the progenitor cells differentiate into erythroid, myeloid, and lymphoid phenotypes (Bertolini et al., Exp Hematol, 24:350, 1997). Hematopoietic stem cells can be purified by flow cytochemistry using monoclonal antibodies, Hoechst 33342 and Rhodamine 123, and can be maintained as non-adherent cells in long-term bone marrow cultures in the presence of cytokines and growth factors. Conversely, bone marrow stromal cells make up the adherent cell layer in long-term in vitro bone marrow cultures and consists of cells of mesenchymal origin that generate cell lines giving rise to fibrous-osteogenic tissues of the skeleton, as well as stromal tissues which support the hematopoietic microenvironment. Marrow stromal cells, operationally called mesenchymal stem cells (MSC) can be isolated by density gradient centrifugation and adherence properties, and exhibit considerable phenotypic plasticity, including fibrogenic, osteogenic, chondrogenic, and adipogenic potential (Pittenger et al., Science, 284:143, 1999). Presumed to serve as an emergency reserve in vivo for crisis situations, the multipotentiality of MSC may also be exploited to therapeutic advantage in the development of autologous cell-based therapies and/or ex vivo gene therapy.

An alternative method has been developed to isolate mesenchymal progenitor cells under stringent survival conditions (Gordon et al., Hum. Gene. Ther., 8:1385, 1997). This technology involves the culture of bone marrow-derived cells on collagen matrices or gels impregnated with a genetically engineered growth factor, i.e., a TGFβ fusion protein bearing an auxiliary collagen-binding domain, under low serum conditions. Interestingly, the binding of TGFβ1 to collagen matrices enhanced its biologic half-life, thus permitting the isolation and expansion of TGFβ1-responsive mesenchymal progenitor cells. This physiological response to the TGFβ1 is both necessary and sufficient for the capture (i.e., survival) of these blastoid cells, which are otherwise not physically separated from either hematopoietic or other mesenchymal cells on the basis of size, density, adherence properties, or cell surface markers. The TGFβ1-responsive cells proliferate readily upon serum reconstitution, and form distinctive colonies within the TGFβ1-vWF impregnated collagen gel. The morphology of these cells is initially blastoid, spherical and non-adherent, not fibroblastic, yet the proliferative cells were capable of overt cytodifferentiation into fibroblastic, chondrogenic and/or osteogenic cells, signifying a mesenchymal precursor. When placed in bone chambers in a subcutaneous rat model, the TGFβ1-responsive mesenchymal progenitor cells formed cartilage in vivo, as well as bone. In contrast, the bone morphogenic protein (BMP)-captured stem cells exhibited a less proliferative and more differentiated osteogenic phenotype in vivo (Andrades et al, Exp. Cell Res., 250:485, 1997).

There is a need for the identification and isolation of progenitor cells capable of giving rise to mesenchymal or hematopoietic stem cells. Further, there is a need for a method of identifying these progenitor cells when present in a population of cells. The identification, and methods for achieving identification, of such cells will have considerable implications for cell biology and gene therapy protocols.

SUMMARY

The present invention provides a molecular marker for the identification of pre-mesenchymal, pre-hematopoietic stem cells. The invention further provides primitive progenitor cells identified by the molecular marker. Such cells have the potential to differentiate into both mesenchymal and hematopoietic phenotypes, as determined by their expression of a molecular marker, by their proliferative response to inductive growth factors and cytokines, and by their morphologic and cytochemical features.

Thus, in one embodiment, the invention provides an isolated pluripotent pre-mesenchymal, pre-hematopoietic progenitor stem cell. In one aspect, a cell of the invention further includes an Osf2 gene expression product. In another aspect, the cell is responsive to a cell proliferation-modulating agent. In a further aspect, the cell is derived from bone marrow tissue.

In another aspect, the invention provides a pharmaceutical composition comprising a therapeutically effective amount of a pluripotent pre-mesenchymal, pre-hematopoietic progenitor stem cell, and a pharmaceutically acceptable carrier or excipient.

In another aspect, the invention provides a method for ameliorating a connective tissue-related disorder in a subject, comprising administering to the subject a therapeutically effective amount of an isolated, pluripotent pre-mesenchymal, pre-hematopoietic stem cell in a pharmaceutically acceptable carrier.

In yet another aspect, the invention provides a method for ameliorating a blood tissue-related disorder in a subject comprising administering to the subject a therapeutically effective amount of a pluripotent pre-mesenchymal, pre-hematopoietic stem cell in a pharmaceutically acceptable carrier.

In another aspect, the invention provides a method for promoting bone marrow tissue regeneration in a subject comprising administering to the subject a therapeutically effective amount of a pluripotent pre-mesenchymal, pre-hematopoietic stem cell, wherein the cell promotes bone marrow regeneration in the subject.

In another embodiment, the invention provides a method for identifying a pre-mesenchymal, pre-hematopoietic stem cell from a population of cells by obtaining a population of cells from an animal species; culturing the cells in vitro; contacting the cells with a cell proliferation modulating agent that induces osteoblast specific factor 2 (Osf2) expression; and identifying a pre-mesenchymal, pre-hematopoietic stem cell that expresses Osf2. In one aspect, Osf2 expression is monitored by detecting Osf2 RNA. In another aspect, Osf2 expression is monitored by detecting an Osf2 polypeptide.

In a further aspect, the present invention provides a pre-mesenchymal, pre-hematopoietic stem cell identified by a method of the invention.

In another aspect, the invention provides a method for identifying a pre-mesenchymal, pre-hematopoietic stem cell from a population of cells by obtaining a population of cells from an animal species; culturing the cells in vitro; contacting the cells with a cell proliferation modulating agent that induces the expression of Osf2; introducing a genetic construct comprising a nucleic acid sequence encoding a detectable marker operably associated with an Osf2 regulatory region; and identifying the cells which express the detectable marker, wherein the expression of the detectable marker is indicative of a pre-mesenchymal, pre-hematopoietic stem cell.

In another embodiment, the present invention provides a kit useful for the detection of a pre-mesenchymal, pre-hematopoietic stem cell comprising two or more containers, wherein a first container that contains a fusion polypeptide comprising a collagen binding domain and a cell proliferation modulating agent; and a second container that contains an Osf2-specific probe. In one aspect, the Osf2-specific probe binds to Osf2 RNA. In another aspect, the Osf2-specific probe binds to an Osf2 polypeptide.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
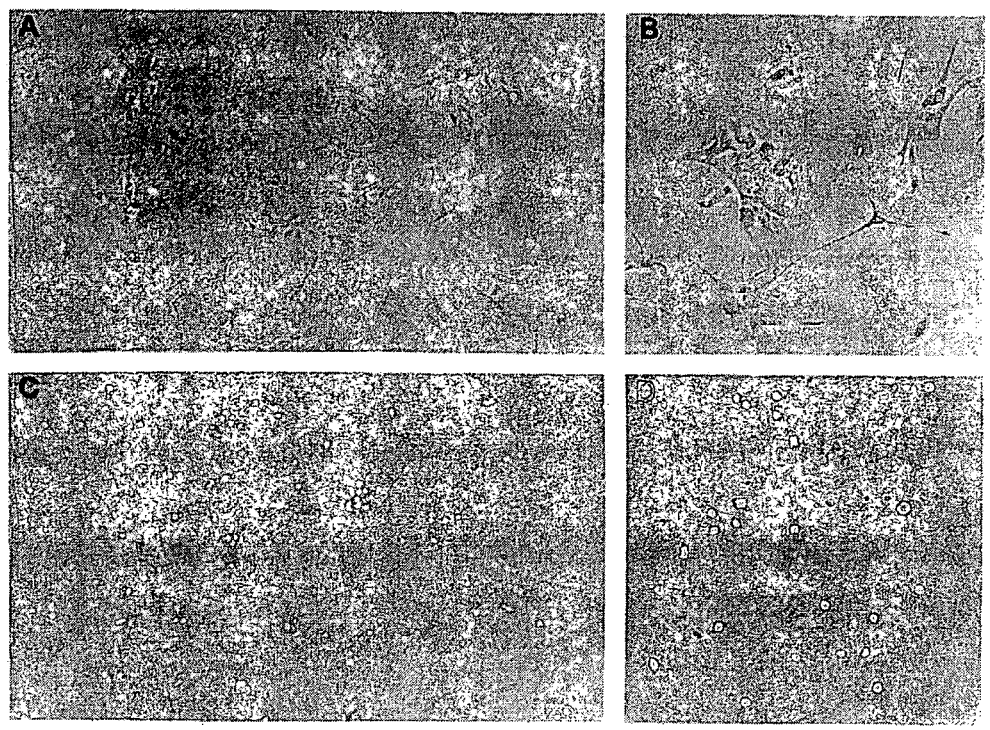
FIG. 1 provides photographs showing a morphological comparison of bone marrow-derived mesenchymal stem cells and TGFβ1-selected pre-mesenchymal stem cells. Panel A shows adherent mesenchymal stem cells. Panel B shows the characteristic fibroblastic phenotype of adherent mesenchymal stem cells. In contrast, TGFβ1-selected stem cells from bone marrow aspirates (Panel C) exhibit a spherical blastoid phenotype with a high nuclear-to-cytoplasm ratio (Panel D).

The present invention provides a molecular marker useful for distinguishing primitive pre-mesenchymal, pre-hematopoietic progenitor stem cells from mesenchymal or hematopoietic stem cells. Such a molecular marker is useful for identifying primitive pre-mesenchymal, pre-hematopoietic stem cells. The present invention further provides a stem cell that expresses such a molecular marker.

The mesenchymal and hematopoietic stem cell population has been extensively characterized according to physical and antigenic criteria, as well as in a variety of in vitro and in vivo assay systems. Despite significant strides in the identification of cytokines that can act on stem cells, it has not been possible isolate primitive stem cell (i.e., progenitor) capable of giving rise to a mesenchymal or hematopoietic stem cell. Similarly, it has not been possible to direct differentiation along lineage-specific pathways. These limitations have hampered the elucidation of regulatory mechanisms which mediate the most fundamental aspect of stem cell biology; that is, the decision to self-renew or commit to differentiation. As a consequence, very little is known about the molecular biology of the most primitive pre-mesenchymal, pre-hematopoietic stem cell in any organism.

Hematopoietic stem cells (HSCs) are the formative pluripotential blast cells found inter alia in bone marrow and peripheral blood that are capable of differentiating into the specific types of hematopoietic or blood cells, such as erythrocytes, lymphocytes, macrophages, and megakaryocytes. After mobilization of HSCs from bone marrow by administration of certain factors, such as G-CSF and W-CSF and subsequent recovery from peripheral blood, HSCs have also come to be referred to as peripheral blood progenitor cells (PBPCs).

Mesenchymal stem cells (MSCs) are the formative pluripotential blast cells found inter alia in bone marrow, blood, dermis and periosteum that are capable of differentiating into more than one specific type of mesenchymal or connective tissue (e.g., adipose, osseous, stroma, cartilaginous, elastic, and fibrous connective tissues) depending upon various influences from bioactive factors, such as cytokines. The potential to differentiate into cells such as osteoblasts and chondrocytes is retained after isolation and expansion in culture; differentiation occurs when the cells are induced in vitro under specific conditions or placed in vivo at the site of damaged tissue.

In one embodiment, the invention provides an isolated pluripotent pre-mesenchymal, pre-hematopoietic stem cell capable of differentiating into either mesenchymal or hematopoietic tissue. The progenitor cell, designated P4 stem cell, has great potential for gene therapy of hematopoietic disorders, muscular dystrophy, connective tissue disorders, lipid storage disorders, skeletal disorders, and bone marrow transplantation, as well as potential reconstitution of the diseased immune system.

As used herein, "isolated" refers to cell fractions isolated from an animal or a human and purified up to at least about 10%, preferably at least about 30%, more preferably at least about 50%, and most preferably at least about 60%, such as about 80%. In a particular embodiment of this aspect of the invention, the purity of the isolated cells is close to 100%, such as about 90%. In such a cell population having a purity of about 90%, perhaps only about 4% of the stem cells clearly act as "active" stem cells, but the rest of the stem cells are quiescent although they may have the ability to be transformed into such "active" stem cells. An "active" stem cell is defined as a cell that undergoes self-renewal and is multipotent. In the context of the present invention, "isolated" preferably refers to removal of at least one cell type from a plurality or mixed population of cells such that an enrichment of a population of cells for a desired cell type is accomplished.

As used herein, a "pre-mesenchymal, pre-hematopoietic stem cell" is a cell that can give rise to blood cells, such as erythrocytes, lymphocytes, macrophages, and megakaryocytes or connective tissue cells, such as adipose, osseous, stroma, cartilaginous, elastic, and fibrous connective tissues. A pre-mesenchymal, pre-hematopoietic cell can be identified, for example, by expression of Osf2 RNA and/or polypeptide.

As used herein, a "pluripotent cell" is a cell that may be induced to differentiate, in vivo or in vitro, into at least two different cell types. These cell types may themselves be pluripotent, and capable of differentiating in turn into further cell types, or they may be terminally differentiated, that is, incapable of differentiating beyond their actual state.

Pluripotent cells include totipotent cells, which are capable of differentiating along any chosen developmental pathway. For example, embryonal stem cells (Thomson et al., Science, 282:1145, 1998) are totipotent stem cells. Pluripotent cells also include other, tissue-specific stem cells, such as hematopoietic stem cells, mesenchymal stem cells, neuronal stem cells, neuroectodermal cells, ectodermal cells, and endodermal cells, for example, gut endodermal cells and mesodermal stem cells which have the ability to give muscle or skeletal components, dermal components, such as skin or hair, blood cells, etc. "Developmental pathway" refers to a common cell fate that can be traced from a particular precursor cell. Thus, for example, the pre-mesenchymal, pre-hematopoietic stem cells of the present invention can give rise to blood cells or connective tissue cells. Thus, the progenitor cells identified by the method of the invention are more primitive, i.e., less fated to a particular developmental pathway than mesenchymal stem cells or hematopoietic stem cells.

A "partially committed" cell is a cell type that is no longer totipotent but remains pluripotent. For example, under the appropriate conditions, progenitor cells of the invention are capable of giving rise to mesenchymal or hematopoietic cells.

Pluripotent cells may be "selected" by any one or more of a variety of means, and the term includes dissection of tissue types from developing embryos, isolation or generation of pluripotent, including totipotent, cells in vivo or in vitro. Preferably, the term refers to the isolation of one class of pluripotent cells from one or more other cell types. In the context of the present invention, the cell can further include an Osf2 gene expression product, thus allowing greater precision in selection using expression of an Osf2 gene product as a molecular marker. For example, the Osf2 gene expression product can be RNA encoding an Osf2 polypeptide. Alternatively, the Osf2 gene expression product can be an Osf2 polypeptide.

Pre-mesenchymal, pre-hematopoietic cells of the invention are responsive to a cell proliferation-modulating agent. As used herein, a "cell proliferation-modulating agent" is any agent that can promote or inhibit cell growth or differentiation. Preferably, a cell proliferation-modulating agent of the invention is a polypeptide. More preferably, the polypeptide is a fusion polypeptide comprising a collagen binding domain and a growth factor, or active fragment thereof.

The term "growth factor," as used herein, includes those molecules that function as growth simulators (mitogens) or as growth inhibitors (sometimes referred to as negative growth factors). Growth factors are also known to stimulate cell migration (e.g., mitogenic cytokines), function as chemotactic agents, inhibit cell migration or invasion of tumor cells, modulate differentiated functions of cells, be involved in apoptosis, and promote survival of cells. Such factors can be secreted as diffusible factors and can also exist in membrane-anchored forms. They can, therefore, act in an autocrine, paracrine, juxtacrine, or retrocrine manner. A cytokine is one type of growth factor. A "cytokine" is polypeptide that acts as a humoral regulator at nano-to-picomolar concentrations and which, either under normal or pathological conditions, can modulate the functional activities of individual cells and tissues. A cytokine can mediate interactions between cells directly and/or can regulate processes taking place in the extracellular environment. Cytokines comprise interleukins, lymphokines, monokines, interferons, colony-stimulating factors, and chemokines, in addition to a variety of other proteins.

A "growth factor-responsive" cell, as used herein, refers to those cells that, when contacted by a cytokine, for example, continue to survive under cell culture conditions not conducive to survival by cells that are unresponsive to the growth factor.

Growth factors further include epidermal growth factors (EGFs), transforming growth factors (TGFs), platelet-derived growth factors (PDGFs), fibroblast growth factors (FGFs), hepatocyte growth factors (HGFs), hemopoietic growth factors (HeGFs), tumor necrosis factor (TNF-alpha), platelet-derived endothelial cell growth factor (PD-ECGF), insulin-like growth factor (IGF), interleukin-8, growth hormone, angiopoietin, vascular endothelial growth factor (VEGF), acidic and basic fibroblast growth factors (FGFs), transforming growth factor alpha (TGF-$\alpha$), and CYR 61 (Babic et al., Proc. Natl. Acad. Sci. USA, 95:6355, 1998;

Kireeva et al., Mol. Cell. Biol., 16:1326, 1996). Such factors further include insulin, IGF-I, IGF-II, nerve growth factor, NGF receptor, EGF, TGF-α, EGF receptor, neu, TGF-$β_1$, TGF-$β_2$, TGF-$β_3$, inhibin α, inhibin β, Müllerian inhibitory substance, TNF-α/β, TNF-receptor (type 1), TNF-receptor (type 2), PDGF A-chain, PDGF B-chain, PDGF receptor α, PDGF receptor β, a-FGF, b-FGF, wnt-2, hst/ks3, hepatocyte growth factor, HGF receptor (c-met), IL-1α/β, (α-chains) IL-2, IL-3, IL-4, IL-5, IL-6, IL-7, IL-9, IL-11, IL-12A (p35), IL-12B (p40), Interleukin 1 (type 1), Interleukin-2α, Interleukin-2β, Interleukin-4, Interleukin-5α, Interleukin-6, Interleukin-7, M-CSF (also called CSF-1), M-CSF receptor (c-fms), GM-CSF, GM-CSF receptor α, GM-CSF receptor β, G-CSF, G-CSF receptor, stem cell factor, SCF receptor (c-kit), Erythropoietin (epo), epo receptor, and Leukemia inhibitory factor. Each of these molecules has been shown to induce cell proliferation, cell growth or differentiation in vivo. Other similar molecules that display cell growth or differentiation modulating activity are the heparin binding growth factors (HBGFs).

A "fusion polypeptide" is a polypeptide containing portions of amino acid sequence derived from two or more different proteins, or two or more regions of the same protein that are not normally contiguous. A "collagen-binding domain" is any polypeptide, or portion thereof, that can bind collagen. Several collagen-binding domains are known in the art (Cruz, M. A. et al., J. Biol. Chem., 270:10822, 1995; Hoylaerts, M. F. et al., Biochem. J., 324:185, 1997; Lankhof, H. et al., Thrombos Haemostas, 75;950, 1996). In one embodiment, the collagen binding domain is the collagen binding domain of von Willebrand factor, which is involved in the recognition of exposed vascular collagen (Takagi, J. et al., Biochemistry 32:8530, 1992; Tuan, T. L. et al., Conn. Tiss. Res., 34:1, 1996; Gordon, E. M. et al., Hum. Gene Ther., 8:1385, all herein incorporated by reference). von Willebrand factor was initially identified as a hemostatic factor in studies of inherited hemophilias (Wagner, Ann., Rev. Cell. Biol., 6:217, 1990), and has been shown to perform a vital surveillance function by targeting platelet aggregates to vascular lesions (Ginsburg and Bowie, Blood, 79:2507, 1992). The decapeptide WREPSFMALS (SEQ ID NO: 1) has been identified to be key in the binding of von Willebrand's factor to collagen (Takagi, J. et al., supra, 1992; Tuan, T. L. et al., supra, 1996). Assays to identify collagen-binding domains of use in the subject invention are known in the art (Takagi, J. et al., supra, 1992; Tuan, T. L. et al., supra, 1996).

The invention further relates to an isolated pluripotent pre-mesenchymal, pre-hematopoietic progenitor stem cell capable of maintaining an undifferentiated state when cultured under conditions that do not induce differentiation or cell death.

The invention further relates to a preparation comprising pre-mesenchymal, pre-hematopoietic progenitor stem cells derived from bone marrow tissue, for example. Such a preparation can be obtained by any of the isolation methods disclosed herein. Such preparations comprise at least about 10%, such as 10-50%, e.g., about 35%, or in the preferred embodiment, up to about 90%, or most preferably an essentially pure culture, of pre-mesenchymal, pre-hematopoietic stem cells. Preferably, at least about 4% of these cells are fully active stem cells. Higher concentrations are possible to obtain, depending on the screening method chosen. Such procedures have never been obtained an isolated population of pre-mesenchymal, pre-hematopoietic stem cells since the identity and characteristics (for example, expression of a specific molecular marker) of the cell have been unknown before the present invention. Thus, in practice, the present method yields the desired concentration of a cell type, i.e., the pre-mesenchymal, pre-hematopoietic stem cells disclosed herein, that has never been identified and/or localized before. In a specific embodiment, the product consists of about 90-95% of pre-mesenchymal, pre-hematopoietic stem cells. In one advantageous embodiment, the product of the method is a cell fraction consisting almost entirely, that is, about 100%, of the pre-mesenchymal, pre-hematopoietic stem cells. Accordingly, the present invention also relates to isolated pre-mesenchymal, pre-hematopoietic stem cells obtainable by the method according to the present invention, as well as to any fraction of isolated pre-mesenchymal, pre-hematopoietic stem cells.

In another aspect, the invention provides a method to facilitate regeneration of blood cells and/or connective tissue in a subject in need of such treatment. For example, stromal tissue is a relatively heterogeneous collection of loose and dense connective tissues distributed throughout the body. The marrow stroma, which is derived from mesenchymal stem cells, provides the scaffolding and soluble factors necessary to support blood cell synthesis, i.e., hematopoiesis. During intensive radiation and chemotherapy treatment bone marrow tissue is depleted or destroyed in a subject. The introduction into the subject of pre-mesenchymal, pre-hematopoietic progenitor cells of the invention can increase survival and decrease the time needed for blood and marrow cell regeneration. Thus, the cells of the invention can be transplanted into a subject in order to regenerate, for example, blood and bone marrow tissue.

The present invention provides a method for enhancing the regeneration of bone marrow tissue through cell transplantation of pre-mesenchymal, pre-hematopoietic progenitor stem cells of the invention. The cells of the invention may be derived from the bone marrow or from peripheral blood. The method for enhancing pre-mesenchymal, pre-hematopoietic progenitor cell engraftment comprises administering to an individual in need thereof, pre-mesenchymal, pre-hematopoietic progenitor cells, wherein said pre-mesenchymal, pre-hematopoietic progenitor stem cells are administered in an amount effective to promote regeneration of bone marrow in the individual.

The treatment of cancer by x-irradiation or alkylating therapy destroys the bone marrow microenvironment as well as the hematopoietic stem cells. Progenitor stem cells of the invention have the ability to give rise to both mesenchymal and hematopoietic stem cells. As a result, the present invention is directed to the advantages of transplanting isolated pre-mesenchymal, pre-hematopoietic progenitor cells to accelerate the process of stromal reconstitution and ultimately marrow engraftment.

Modes of administration of the pre-mesenchymal, pre-hematopoietic stem cell preparation include, but are not limited to, systemic intravenous injection and injection directly to the intended site of activity. The preparation can be administered by any convenient route, for example, by infusion or bolus injection, and can be administered together with other biologically active agents. Administration is preferably systemic.

The present invention also provides pharmaceutical compositions comprising a therapeutically effective amount of the stem cells of the present invention and a pharmaceutically acceptable carrier or excipient. Such a carrier includes, but is not limited to, saline, buffered saline, dextrose, water, and combinations thereof. The formulation should suit the mode of administration.

In a preferred embodiment, the pre-mesenchymal, pre-hematopoietic stem cell preparation or composition is formulated in accordance with routine procedures as a pharmaceutical composition adapted for intravenous administration to human beings. Typically, compositions for intravenous administration are solutions in sterile isotonic aqueous buffer. Where necessary, the composition may also include a local anesthetic to ameliorate any pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Cells of the invention can also be delivered to a targeted site by any delivery system suitable for targeting cells to a particular tissue. For example, the cells can be encapsulated in a delivery vehicle that allows for the slow release of the cell(s) at the targeted site. The delivery vehicle can be modified such that it is specifically targeted to a particular tissue. The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bound to the surface of the targeted delivery system will be ligands and receptors which will allow the targeted delivery system to find and "home in" on the desired cells. A ligand may be any compound of interest that will bind to another compound, such as a receptor.

For example, a colloidal dispersion system can be used in the present invention. Colloidal dispersion systems include macromolecule complexes, nanocapsules, microspheres, beads, and lipid-based systems, including oil-in-water emulsions, micelles, mixed micelles, and liposomes. The preferred colloidal system of this invention is a liposome. Liposomes are artificial membrane vesicles that are useful as delivery vehicles in vitro and in vivo. It has been shown that large unilamellar vesicles (LUV), which range in size from 0.2-4.0 μm can encapsulate a substantial percentage of a aqueous buffer containing large macromolecules.

The method of the invention can be altered, particularly by: (1) increasing or decreasing the amount of pre-mesenchymal, pre-hematopoietic stem cells injected; (2) varying the number of injections; (3) varying the method of delivery of the cells; or (4) varying the source of pre-mesenchymal, pre-hematopoietic stem cells. Although cells derived from the bone marrow of the subject being treated is preferable, the pre-mesenchymal, pre-hematopoietic stem cells can be obtained from other individuals or species, or from genetically engineered inbred donor strains, or from in vitro cell culture.

The pre-mesenchymal, pre-hematopoietic stem cell preparation is used in an amount effective to promote engraftment of mesenchymal and/or hematopoietic stem cells in the recipient. The pre-mesenchymal, pre-hematopoietic stem cell preparation preferably is administered either intravenously one to three times per day, and may be adjusted to meet optimal efficacy and pharmacological dosing.

Accordingly, the invention relates to a pharmaceutical preparation comprising at least one pre-mesenchymal, pre-hematopoietic stem cell according to the invention and a pharmaceutically acceptable carrier. The preparations according to the invention may be adapted for injection into a suitable part of, for example, a bone. Such a pharmaceutical preparation comprises any suitable carrier, such as an aqueous carrier, e.g., buffered saline etc. The active composition of the present preparation is generally sterile and free of any undesirable matter. In addition, the preparations may contain pharmaceutically acceptable auxiliary substances as required to approximate physiological conditions, such as pH adjusting agents, etc. The concentration of the present pre-mesenchymal, pre-hematopoietic stem cell in the preparation will vary depending on the intended application thereof, and the dosages thereof are decided accordingly by the patient's physician. The stem cells used may have been isolated by the present method or any other suitable method or obtained in any other way. In a preferred embodiment, the present stem cell may have been genetically manipulated in order to be especially adapted for the intended use thereof.

In a further aspect, the cells of the invention can be administered to a patient wherein such administration is therapeutically useful. Alternatively, the cells of the invention can be used to replace or supplement the corresponding cell type in a patient by administration of the cells of the invention. The cells of the invention may be used to coat implants, thus acting as a barrier between the implant and the patient. Administration of the cells of the invention is achieved by methods known to those skilled in the art.

In another aspect, the invention provides a method for ameliorating a connective tissue-related disorder in a subject, comprising administering to the subject a therapeutically effective amount of an isolated, pluripotent pre-mesenchymal, pre-hematopoietic stem cell in a pharmaceutically acceptable carrier. In a related aspect, the invention provides a method for ameliorating a blood tissue-related disorder in a subject, comprising administering to the subject a therapeutically effective amount of a pluripotent pre-mesenchymal, pre-hematopoietic stem cell in a pharmaceutically acceptable carrier. Connective tissue and blood tissue-related disorders include, but are not limited to, muscular dystrophy, a lipid storage disorder, a skeletal disorder, or bone marrow disorder, as well as potential reconstitution of the diseased immune system.

The term "ameliorate" denotes a lessening of the detrimental effect of the disease-inducing response in the patient receiving therapy. For example, where the disorder is due to a diminished amount of growth of connective tissue or blood tissue cells, a stem cell of the invention can be contacted with the site of the disorder.

The terms "treating," "treatment," and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder. "Treating" as used herein covers any treatment of a disorder in a mammal, and includes:

(a) preventing a disorder from occurring in a subject that may be predisposed to a disorder, but has not yet been diagnosed as having it;
(b) inhibiting a disorder, i.e., arresting its development; or
(c) relieving or ameliorating the disorder, e.g., cause regression of the disorder.

The methods include administering to the subject a pharmaceutically effective amount of a pre-mesenchymal, pre-hematopoietic progenitor stem cell of the invention. In general, such a method is based on administration of a pre-mesenchymal, pre-hematopoietic progenitor stem cell according to the invention with an unimpaired function and ability to produce blood tissue, connective tissue, or other cell types depending on the disorder.

Accordingly, the cells of the present invention can be transplanted into a patient for the treatment of disease or injury by any method known in the art that is appropriate for the transplant site.

Methods of administration of the cells of the invention include, but are not limited to, intradermal, intramuscular, intraperitoneal, intravenous, subcutaneous, intranasal, and epidural routes. The cells of the invention may be administered by any convenient route, for example, by infusion or bolus injection, by absorption through epithelial or mucocutaneous linings (e.g., oral mucosa, rectal and intestinal mucosa, etc.), and may be administered together with other biologically active agents. Administration can be systemic or local.

It may be desirable to administer the cells of the invention locally to the area in need of treatment; this may be achieved by, for example and not by way of limitation, local infusion during surgery, topical application (e.g., in conjunction with a wound dressing after surgery), by injection, by means of a catheter, or by means of an implant, said implant being of a porous, non-porous, or gelatinous material, including membranes, such as sialastic membranes, or fibers.

In another aspect, the pre-mesenchymal, pre-hematopoietic stem cells prepared by the present method can be genetically modified. Manipulations may be performed in order to modify various properties of the cell, e.g., to render it more adapted or resistant to certain environmental conditions, to induce a production of one or more certain substances therefrom, which substances may, e.g., improve the viability of the cell, or alternatively may be useful as drugs or medicaments. Some such genetic alterations may be performed in order to make the cell more suitable for use in transplantation, for example, in order to avoid rejection thereof from the recipient (for reviews of gene therapy procedures, see Anderson, Science, 256:808; Mulligan, Science, 926; Miller, Nature, 357: 455; Van Brunt, Biotechnology, 6(10):1149; and Yu et al., Gene Therapy, 1:13). Thus, the present invention also encompasses gene therapy methods, wherein, pre-mesenchymal, pre-hematopoietic stem cells are used, as well as preparations intended to be used in such methods comprising the cells according to the invention. Such gene therapy methods may be used to treat and/or prevent any conditions wherein blood or connective tissue requires repair, replacement, or augmentation. For example, a vector can be used to transfer a genetic element to a cell of the invention such that the cell is modified to express a nucleic acid or protein beneficial to the treatment of a pathological disorder. Alternatively, the vector can be used to knock-out the function of a particular nucleic acid sequence that is native to the stem cell of the invention.

A "vector" refers to a recombinant DNA or RNA construct, such as a plasmid, a phage, recombinant virus, or other vector that, upon introduction into a appropriate host cell of the invention, results in a modification of a pre-mesenchymal, pre hematopoietic stem cell. Appropriate expression vectors are well known to those with ordinary skill in the art and include those that are replicable in eukaryotic and/or prokaryotic cells and those that remain episomal or those that integrate into the host cell genome.

Construction of vectors according to the invention employs conventional techniques, for example, as described in Sambrook et al., 1989. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing gene expression and function are known to those skilled in the art. Gene presence, amplification, and/or expression may be measured in a sample directly, for example, by conventional Southern blotting, Northern blotting to quantitate the transcription of mRNA, dot blotting (DNA or RNA analysis), or in situ hybridization, using an appropriately labeled probe which may be based on a sequence provided herein. Those skilled in the art will readily envisage how these methods may be modified, if desired.

Method for Identifying a P4 Progenitor Cell

In another embodiment, the invention provides a method for identifying a pre-mesenchymal, pre-hematopoietic stem cell from a population of cells, comprising obtaining a population of cells from an animal species; culturing the cells in vitro; contacting the cells with a cell proliferation-modulating agent that induces osteoblast specific factor 2 (Osf2) expression; and identifying a pre-mesenchymal, pre-hematopoietic stem cell that expresses osteoblast specific factor 2 (Osf2). The method of the invention is useful for identifying a postnatal mesodermal stem cell that can be harvested from bone marrow aspirates, expanded in culture, and stimulated to differentiate into either blood or bone/connective tissue elements.

"Identifying," as used herein, refers to the detection of a pluripotent stem cell in a population of cells. A "population of cells" can consist of a heterogenous mixture or plurality of different cell types in a particular sample. Alternatively, a "population of cells" can be homogenous in that the cells are the same. Preferably, cells useful in the method of the invention are bone marrow-derived cells.

The method of the invention includes culturing the population of cells in vitro and contacting the cells with a cell proliferation-modulating agent that induces osteoblast specific factor 2 (Osf2) expression. As used herein, "culturing" cells of the invention includes the methods described below for growing pre-mesenchymal, pre-hematopoietic stem cells. However, it is understood that any method of culturing such stem cells that allows for the expression of an Osf2 gene product is encompassed by the method of the invention. Preferably, the agent is a fusion polypeptide comprising a collagen binding domain and a growth factor, or fragment thereof, as previously described.

Suitable pluripotent stem cells may be derived from a number of sources. For example, ES cells, such as human ES cells and cells derived from Germ cells (EG cells) may be derived from embryonal tissue and cultured as cell lines (Thomson et al., Science, 282:1145, 1998). Alternatively, pluripotent cells may be prepared by a retrodifferentiation, by the administration of growth factors or otherwise, or by cloning, such as by nuclear transfer from an adult cell to a pluripotent cell such as an ovum. Human stem cells of specific lineages may be isolated from human tissues directly. Alternatively, stem cells from non-human animals, such as rodents, may be used. Preferably, the pluripotent stem cells of the invention are derived from bone marrow tissue.

The invention includes methods for identifying Osf2 expression by screening a sample having, or believed to have, an Osf2 expression product. As used herein, an "Osf2 gene expression product" is any molecule derived from the coding sequence of the Osf2 gene. For example, an Osf2 gene expression product can be a nucleic acid molecule that encodes the Osf2 polypeptide, or the polypeptide itself, or a fragment thereof.

In these methods, a sample, e.g., bone-marrow-derived cells, that contains a nucleic acid encoding an Osf2 polypeptide or the Osf2 polypeptide itself, is screened with an Osf2-specific probe, e.g., a Osf2-specific nucleic acid probe or an antibody to an Osf2 polypeptide.

In one aspect, the term "Osf2-specific probe," in the context of this method of invention, refers to probes that bind to nucleic acids encoding Osf2 polypeptides or to complementary sequences thereof. Osf2-specific nucleic acid probes can be nucleic acid molecules (e.g., molecules containing DNA or RNA nucleotides, or combinations or modifications thereof) that specifically hybridize to nucleic acids encoding Osf2 polypeptides, or to complementary sequences thereof.

Expression of the Osf2 gene can be detected by contacting a sample containing nucleic acid encoding an Osf2 polypeptide with a nucleic acid probe. The sequence of the probe can be derived from nucleic acid molecules that encode Osf2 polypeptides (and fragments thereof) and related nucleic acids, such as: (1) nucleic acids containing sequences that are complementary to, or that hybridize to, nucleic acids encoding Osf2 polypeptides, or fragments thereof (e.g., fragments containing at least 10, 12, 15, 20, or 25 nucleotides); and (2) nucleic acids containing sequences that hybridize to sequences that are complementary to nucleic acids encoding Osf2 polypeptides or fragments thereof (e.g., fragments containing at least 10, 12, 15, 20, or 25 nucleotides) can be used in methods focused on their hybridization properties. For example, as is described in further detail below, such nucleic acid molecules can be used in the following methods: PCR methods for synthesizing Osf2 nucleic acids, methods for detecting the presence of an Osf2 nucleic acid in a sample, screening methods for identifying nucleic acids encoding new Osf2 family members, or RT-PCR methods for identifying an Osf2 transcript in a sample. oligonucleotide probes useful for screening methods are from 10 to about 150 nucleotides in length. Further, such probes are preferably 10 to about 100 nucleotides in length, and more preferably from 10 to about 50 nucleotides in length.

Methods for obtaining such probes can be designed based on the amino acid sequence known in the art for Osf2. The probes, which can contain at least 10, e.g., 15, 25, 35, 50, 100, or 150 nucleotides, can be produced using any of several standard methods.

Screening procedures that rely on nucleic acid hybridization make it possible to isolate any gene sequence or RNA derived therefrom from any organism, provided the appropriate probe is available. For example, oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest is present. In other words, by using selective hybridization conditions directed to avoid non-specific binding, it is possible, for example, to allow the autoradiographic visualization of a specific cDNA clone by the hybridization of the target DNA to that single probe in the mixture which is its complete complement (Wallace et al., Nucleic Acid Research, 9:879, 1981). It is also appreciated that such selective hybridization probes can be, and are preferably, labeled with an analytically detectable reagent to facilitate identification of the probe. Useful reagents include, but are not limited to, radioactivity, fluorescent dyes, or enzymes capable of catalyzing the formation of a detectable product. The selective hybridization probes are thus useful to isolate complementary copies of DNA from other sources or to screen such sources for related sequences.

With respect to nucleic acid sequences that hybridize to specific nucleic acid sequences disclosed herein, hybridization may be carried out under conditions of reduced stringency, medium stringency, or even stringent conditions. As an example of oligonucleotide hybridization, a polymer membrane containing immobilized denatured nucleic acid is first prehybridized for 30 minutes at 45° C. in a solution consisting of 0.9 M NaCl, 50 mM NaH2PO4, pH 7.0, 5.0 mM Na$_2$EDTA, 0.5% SDS, 10× Denhardt's, and 0.5 mg/mL polyriboadenylic acid. Approximately $2 \times 10^7$ cpm (specific activity of $4 \times 10^8$ cpm/µg) of $^{32}$P end-labeled oligonucleotide probe are then added to the solution. After 12-16 hours of incubation, the membrane is washed for 30 minutes at room temperature in 1× SET (150 mM NaCl, 20 mM Tris hydrochloride, pH 7.8, 1 mM Na$_2$EDTA) containing 0.5% SDS, followed by a 30 minute wash in fresh 1× SET at Tm-10° C. for the oligonucleotide probe. The membrane is then exposed to auto-radiographic film for detection of hybridization signals.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA vs. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each in the order listed above, repeating any or all of the steps listed. However, as mentioned above, optimal conditions will vary, depending on the particular hybridization reaction involved, and can be determined empirically.

It is also appreciated that such probes can be, and are preferably, labeled with an analytically detectable reagent to facilitate identification of the probe. Useful reagents include, but are not limited to, radioactivity, fluorescent dyes, or proteins capable of catalyzing the formation of a detectable product. The probes are thus useful to isolate complementary copies of DNA from other animal sources or to screen such sources for related sequences.

In another aspect, the term "Osf2-specific probe," in the context of this method of invention, refers to probes that bind to Osf2 polypeptides, or fragments thereof. For example, a polyclonal or monoclonal antibody can be used to detect the presence of Osf2 in a sample, thereby indicating the presence of a pre-mesenchymal, pre-hematopoietic stem cell. For preparation of monoclonal antibodies, any technique that provides antibodies produced by continuous cell line cultures can be used. Examples include the hybridoma technique (Kohler et al., Nature, 256:495, 1975), the trioma technique, the human B-cell hybridoma technique (Kozbor et al., Immunology Today, 4:72, 1983), and the EBV-hybridoma technique to produce human monoclonal antibodies (Cole et al., Monoclonal Antibodies and Cancer Therapy, Alan R. Liss, Inc., pp. 77-96, 1985).

According to another aspect of the invention, a genetic construct comprising a nucleic acid sequence encoding a detectable marker operably associated with an Osf2 regulatory region is introduced into a population of cells. Expression of the detectable marker is indicative of a pre-mesenchymal, pre-hematopoietic stem cell. Thus, pre-mesenchymal, pre-hematopoietic stem cells can be actively sorted from other cell types by detecting the expression of Osf2 polypeptides in vivo using a reporter system.

Osf2 is a transcriptional activator that activates transcription from a Osf2-specific regulatory region. Thus, for example, the invention provides a method for isolating a desired cell type from a population of cells, comprising introducing a genetic construct comprising a coding sequence encoding a detectable marker operably associated with an Osf2 regulatory region into a population of cells; detecting the cells which express the detectable marker; and sorting the cells which express the detectable marker from the population of cells. Thus, the identification of Osf2 gene expression as a molecular marker of pre-mesenchymal, pre-hematopoietic stem cells provides an opportunity for the detection of such cells prior to their differentiation into a mesenchymal or a hematopoietic cell.

The detectable marker may be any entity that provides a means for distinguishing Osf2-expressing cells from those cells not expressing Osf2. Such markers include those that can be selected with drugs, such as antibiotics. A detectable marker can also include a radioactive marker. Preferably a detectable marker of the invention is a fluorescent or luminescent marker that may be detected and sorted by automated cell sorting approaches. For example, the marker may be GFP or luciferase. Other useful markers include those that are expressed in the cell membrane, thus facilitating cell sorting by affinity means.

An "Osf2 regulatory region" comprises nucleic acid sequences derived from genes that are regulated or controlled by Osf2 polypeptides. Osf2 control sequences are known in the art.

A genetic construct of the invention can be an expression vector capable of expressing nucleic acid encoding a heterologous nucleic acid sequence operably associated with an Osf2 regulatory sequence. The genetic construct according to the invention may comprise any promoter and enhancer elements as required, so long as the overall control remains sensitive to an Osf2 polypeptide. The regulatory sequences responsive to Osf2 polypeptides are known in the art, and have been described in the literature cited herein and are incorporated herein by reference; at least, however, the construct of the invention will comprise an Osf2 binding site. Preferably, the natural Osf2-responsive control elements are used in their entirety; however, other promoter and enhancer elements may be substituted where they remain under the influence of Osf2 expression.

Thus, an expression vector refers to a recombinant DNA or RNA construct, such as a plasmid, a phage, recombinant virus, or other vector that, upon introduction into an appropriate host cell expressing Osf2, results in expression of a detectable marker and the subsequent identification of a pre-mesenchymal, pre hematopoietic stem cell. Appropriate expression vectors are well known to those with ordinary skill in the art and include those that are replicable in eukaryotic and/or prokaryotic cells and those that remain episomal or those that integrate into the host cell genome.

Construction of vectors according to the invention employs conventional techniques, for example, as described in Sambrook et al., 1989. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing gene expression and function are known to those skilled in the art. Gene presence, amplification, and/or expression may be measured in a sample directly, for example, by conventional Southern blotting, Northern blotting to quantitate the transcription of mRNA, dot blotting (DNA or RNA analysis), or in situ hybridization, using an appropriately labeled probe which may be based on a sequence provided herein. Those skilled in the art will readily envisage how these methods may be modified, if desired.

The detectable marker will only be expressed in desired cell types because only these cells express the relevant Osf2 polypeptide, which is required for transcription from the Osf2 control sequences. Preferably, therefore, the expression means used to express the detectable marker are not leaky, and express a minimal amount of the marker in the absence of the Osf2 polypeptide. Techniques for transforming cells with coding genetic constructs according to the invention, detecting the marker, and sorting cells accordingly are known in the art.

As used herein, terms such as "transfection," "transformation," and the like are intended to indicate the transfer of nucleic acid to a cell or organism in functional form. Such terms include various means of transferring nucleic acids to cells, including transfection with CaP04, electroporation, viral transduction, lipofection, delivery using liposomes, and other delivery vehicles, such as biolistics and the like.

Cells can be sorted by affinity techniques or by cell sorting (such as fluorescence-activated cell sorting) where they are labeled with a suitable label, such as a fluorophore conjugated to or part of, for example, an antisense nucleic acid molecule or an immunoglobulin, or an intrinsically fluorescent protein, such as green fluorescent protein (GFP) or variants thereof. As used herein, "sorting" refers to the at least partial physical separation of a first cell type from a second.

Sorting of cells, based upon detection of expression of an Osf2 gene, may be performed by any technique known in the art, as exemplified above. For example, cells may be sorted by flow cytometry or FACS. For a general reference, see Flow Cytometry and Cell Sorting: A Laboratory Manual (1992) A. Radbruch (Ed.), Springer Laboratory, New York.

Flow cytometry is a powerful method for studying and purifying cells. It has found wide application, particularly in immunology and cell biology: however, the capabilities of the FACS can be applied in many other fields of biology. The acronym "FACS" stands for Fluorescence Activated Cell Sorting, and is used interchangeably with "flow cytometry."

The principle of FACS is that individual cells, held in a thin stream of fluid, are passed through one or more laser beams, causing light to be scattered and fluorescent dyes to emit light at various frequencies. Photomultiplier tubes (PMT) convert light to electrical signals, which are interpreted by software to generate data about the cells. Subpopulations of cells with defined characteristics can be identified and automatically sorted from the suspension at very high purity.

FACS machines collect fluorescence signals in one to several channels corresponding to different laser excitation and fluorescence emission wavelengths. Fluorescent labeling allows the investigation of many aspects of cell structure and function. The most widely used application is immunofluorescence: the staining of cells with antibodies conjugated to fluorescent dyes, such as fluorescein and phycoerythrin. This method is often used to label molecules on the cell surface, but antibodies can also be directed at targets within the cell. In direct immunofluorescence, an antibody to a particular molecule, the Osf2 polypeptide, is directly conjugated to a fluorescent dye. Cells can then be stained in one step. In indirect immunofluorescence, the primary antibody is not labeled, but a second fluorescently conjugated antibody is added which is specific for the first antibody: for example, if the anti-Osf2 antibody is a mouse IgG, then the second antibody could be a rat or rabbit antibody raised against mouse IgG.

FACS can be used to measure gene expression of a reporter gene contained in a genetic construct of the invention for the purpose of identifying endogenous Osf2. Examples of reporter genes are P-galactosidase and Green Fluorescent Protein (GFP). P-galactosidase activity can be detected by FACS using fluorogenic substrates, such as fluorescein digalactoside (FDG). FDG is introduced into cells by hypotonic shock, and is cleaved by the enzyme to generate a fluorescent product which is trapped within the cell. One enzyme can therefore generate a large amount of fluorescent product. Cells expressing GFP constructs will fluoresce without the addition of a substrate. Mutants of GFP are available which have different excitation frequencies but which emit fluorescence in the same channel. In a two-laser FACS machine, it is possible to distinguish cells which are excited by the different lasers, and therefore assay two transfections at the same time.

Alternative means of cell sorting may also be employed. For example, the invention comprises the use of nucleic acid probes complementary to Osf2 mRNA. Such probes can be used to identify cells expressing Osf2 polypeptides individually, such that they may subsequently-be sorted either manually or using FACS sorting. Nucleic acid probes complementary to Osf2 mRNA may be prepared using the general procedures as described by Sambrook et al. (1989). Thus, in another embodiment, the invention comprises the use of an antisense nucleic acid molecule, complementary to an Osf2 mRNA, conjugated to a fluorophore which may be used in FACS cell sorting.

Suitable imaging agents for use with FACS may be delivered to the cells by any suitable technique, including simple exposure thereto in cell culture, delivery of transiently expressing nucleic acids by viral or non-viral vector means, liposome-mediated transfer of nucleic acids or imaging agents, and the like.

The invention, in certain embodiments, includes antibodies specifically recognizing and binding to Osf2 polypeptides. For example, such antibodies may be generated against the Osf2 polypeptides having the amino acid sequences set forth above. Alternatively, Osf2 polypeptides or fragments thereof (which may also be synthesized by in vitro methods) are fused (by recombinant expression or an in vitro peptidyl bond) to an immunogenic polypeptide and this fusion polypeptide, in turn, is used to raise antibodies against an Osf2 epitope.

The present invention further provides a method for generating a pre-mesenchymal, pre-hematopoietic stem cell from a progenitor stem cell in a sample, comprising contacting the sample with an Osf2 protein. The invention further provides a method for generating a pre-mesenchymal, pre-hematopoietic stem cell from a progenitor stem cell in a sample, comprising contacting the sample with a nucleic acid encoding Osf2.

The invention provides a molecular marker that is temporally associated with the development of mesenchymal and hematopoietic stem cells. Expression of the Osf2 gene not only provides a means for identifying the progenitor cell of such cells, but also provides an opportunity to control the development of pre-mesenchymal, pre-hematopoietic stem cells into mesenchymal or hematopoietic stem cells. By regulating the expression of Osf2, the transition from pre-mesenchymal, pre-hematopoietic stem cells into mesenchymal or hematopoietic stem cells can be controlled. For example, nucleic acid encoding Osf2 may be inserted into a vector suitable for expression of cDNAs in mammalian cells, e.g., a CMV enhancer-based vector such as pEVRF (Matthias et al., Nucl. Acid Res., 17:6418, 1989).

Alternatively, the invention provides a method for regulating the expression of Osf2 in a progenitor cell, comprising contacting a cell with a polynucleotide that inhibits such expression. Thus, when development of a mesenchymal or hematopoietic stem cell is controllable by regulating the expression of Osf2, a therapeutic approach that directly interferes with the transcription of Osf2 into RNA or the translation of OSF2 mRNA into protein is possible. An "Osf2 target nucleic acid sequence," as used herein, encompasses any nucleic acid encoding an Osf2 protein or fragment thereof. For example, antisense nucleic acid or ribozyme that binds to the Osf2 transcript RNA or cleave it are also included within the invention. Antisense RNA or DNA molecules bind specifically with a targeted gene's RNA message, interrupting the expression of that gene's protein product. The antisense binds to the transcript RNA forming a double-stranded molecule that cannot be translated by the cell. Antisense oligonucleotides of about 15-25 nucleotides are preferred, since they are easily synthesized and have an inhibitory effect just like antisense RNA molecules. In addition, chemically reactive groups, such as iron-linked ethylenediaminetetraacetic acid (EDTA-Fc) can be attached to an antisense oligonucleotide, causing cleavage of the RNA at the site of hybridization. These and other uses of antisense methods to inhibit the in vivo translation of genes are well known in the art (e.g., De Mesmaeker et al., Curr. Opin. Struct. Biol., 5:343, 1995; Gewirtz, A. M. et al., Proc. Natl. Acad. Sci. U.S.A., 93:3161, 1996; Stein, C. A., Chem. and Biol., 3:319, 1997).

"Transcript RNA," as used herein, is RNA that contains nucleotide sequence encoding a protein product. Preferably, the transcript RNA is messenger RNA (mRNA). "mRNA," as used herein, is a single-stranded RNA molecule that specifies the amino acid sequence of one or more polypeptide chains. In addition, transcript RNA can be heterogenous nuclear RNA (hnRNA) or masked RNA. "hnRNA," as the term is used herein, represents the primary transcripts of RNA polymerase II and includes precursors of all messenger RNAs from which introns are removed by splicing. hnRNAs are extensively processed to give mRNA, which is exported to the cytoplasm where protein synthesis occurs. This processing may include the addition of a 5'-linked 7-methyl-guanylate "cap" at the 5' end and a sequence of adenylate groups at the 3' end, the poly A "tail," as well as the removal of any introns and the splicing together of exons. "Masked RNA," as used herein, is any form of mRNA that is present in inactive form. More specifically, masked RNA constitutes a store of maternal information for protein synthesis that is unmasked (derepressed) during the early stages of morphogenesis.

Antisense nucleic acids are DNA or RNA molecules that are complementary to at least a portion of a specific transcript RNA molecule (Weintraub, Scientific American, 262:40, 1990). In the cell, the antisense nucleic acids hybridize to the corresponding transcript RNA, forming a double-stranded molecule. For example, the antisense nucleic acids interfere with the translation of the mRNA, since the cell will not translate an mRNA that is double-stranded. Antisense oligomers of about 15 nucleotides are preferred, since they are easily synthesized and are less likely to cause problems than larger molecules. The use of antisense methods to inhibit the in vitro translation of genes is well known in the art (Marcus-Sakura, Anal. Biochem., 172:289, 1988).

Use of an oligonucleotide to stall transcription is known as the triplex strategy, since the oligomer winds around double-helical DNA, forming a three-strand helix. Therefore, these triplex compounds can be designed to recognize a unique site on a chosen gene (Maher et al., Antisense Res. and Dev., 1(3):227, 1991; Helene, C., Anticancer Drug Design, 6(6):569, 1991).

Ribozymes are RNA molecules possessing the ability to specifically cleave other single-stranded RNA in a manner analogous to DNA restriction endonucleases. Through the modification of nucleotide sequences that encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

There are two basic types of ribozymes, namely, tetrahymena-type (Hasselhoff, Nature, 334:585, 1988) and "hammerhead"-type. Tetrahymena-type ribozymes recognize sequences that are four bases in length, while "hammerhead",-type ribozymes recognize base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species, and 18-based recognition sequences are preferable to shorter recognition sequences. These and other uses of antisense methods to inhibit the in vivo translation of genes are well known in the art.

In another embodiment, the present invention provides a kit useful for the detection of a pre-mesenchymal, pre-hematopoietic stem cell, comprising two or more containers, wherein a first container that contains a fusion polypeptide comprising a collagen binding domain and a cell growth or differentiation modulating agent; and a second container that contains an Osf2-specific binding agent that binds to an Osf2 gene product. In one aspect, the Osf2-specific binding agent binds to an Osf2 RNA. In another aspect, the Osf2 binding agent binds to an Osf2 polypeptide.

According to another aspect of the invention, the ex vivo identified pre-mesenchymal, pre-hematopoietic stem cells are available for therapeutic use. Because the cells have been identified prior to differentiation into a mesenchymal or hematopoietic cell, they are capable of being used therapeutically for the development of connective tissue or blood tissue, as previously described. The cells are available to receive exogenous genes, including by retroviral or other vectors that require a round of replication. Alternatively, the cells are available for transplantation either autologously or heterologously.

It must be noted that as used herein and in the appended claims, the singular forms "a," "and," and "the" include plural referents, unless the context clearly dictates otherwise. Thus, for example, reference to "a target cell" includes a plurality of such cells, and reference to "the expression vector" includes reference to one or more transformation vectors and equivalents thereof known to those skilled in the art, and so forth.

Unless defined otherwise, all technical and scientific terms used herein have the same meaning as commonly understood to one of ordinary skill in the art to which this invention belongs. Although any methods, cells and genes similar or equivalent to those described herein can be used in the practice or testing of the invention, the preferred methods, devices, and materials are now described.

All publications mentioned herein are incorporated herein by reference in full for the purpose of describing and disclosing the cell lines, vectors, and methodologies that are described in the publications that might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Materials and Methods

Genetic Engineering of a Recombinant TGFβ1-Vwf Fusion Protein. A prokaryotic expression vector was engineered to produce a tripartite fusion protein consisting of the cDNA sequence encoding the mature active fragment of human TGFβ1, an auxiliary von Willebrand factor-derived collagen-binding domain, and a 6×His purification tag (TGFβ1-vWF) (Han et al., Protein Expr. Purif., 11:169, 1997). The expressed fusion protein was isolated and purified to homogeneity from E. coli inclusion bodies using nickel chelate chromatography, solubilized with 8M urea, and renatured by oxidative refolding under optimized redox conditions. The biological activity of the TGFβ1-vWF fusion protein was evaluated by in vitro cell proliferation assays (specific activity:~85%) using the commercial TGFβ1 as a standardized control.

Preparation of Collagen Gels. Rat tail tendon type I collagen was prepared as described by Nimni et al. (J. Biomed. Mater. Res., 21:741, 1987). Briefly, rat tail tendons were harvested and rinsed with 1×PBS, followed by pepsin (0.5 mg/ml) digestion overnight, two rounds of 1M NaCl (pH 7.5) precipitation, and dialysis into 0.5 M acetic acid first, then dialysis into 0.001N HCl. The concentration of collagen was determined by hydroxyproline assay; its purity was confirmed by 2-D peptide mapping. 3 mg/ml collagen was diluted three times with 3×DMEM to make 1× collagen solution, the pH was adjusted to 7.5, and aliquots were stored at 4° C. The solid collagen matrices were prepared as described previously by Nimni and co-workers (Biorheology, 17:51, 1980).

Preparation of Cell Population. Bone marrow aspirates were obtained from euthanized 6 week-old, 20 gm B6CBA immunocompetent mice (Jackson Labs, Bar Harbor, Me.). The femoral midshaft bone marrow tissue was washed into DMEM containing penicillin (100 U/ml) and streptomycin (100 μg/ml). Bone marrow was collected by drawing the marrow into syringes fitted with an 18-gauge needle several times. Bone marrow aspirates were layered onto a Percoll gradient, after which a low-density fraction was collected and cultured in D10 medium. Marrow cells cultured under these conditions give rise to fibroblastic colonies. These adherent cells rapidly grow to confluence and are often referred to as marrow fibroblasts. The non-adherent cells were removed by media change after three days, and the remaining cells were allowed to grow to confluence, yielding a population of uniformly fibroblast-like cells with multilineage potential, hence, operationally known as mesenchymal stem cells.

Capture Of TGFβ1-Responsive Stem Cells on TGFβ1-Vwf-Impregnated Collagen Gels. Cells, prepared from murine bone marrow aspirates described above, were pelleted by centrifugation at 1000 RPM for 5 minutes, resuspended in serum-free medium, and counted with a hemocytometer. Washed cell pellets were suspended in 10 μl serum-free medium and 200 μl neutralized collagen, after which 10 μl recombinant TGFβ1-vWF or control medium was added. The cell/collagen mixtures were transferred to 24 well tissue culture plates, and incubated at 37° C. for 30 minutes until the collagen molecules aggregated into fibrils, trapping cells within the collagen gels. Then, 0.5 ml 0.5% FBS in DMEM medium was overlayed on the gel and the cells were incubated at 37° C. for 7 days without changing medium. After 7 days of serum deprivation, the medium was replaced with DMEM-10% FBS (D10), and medium was changed every 3 days. When cells prepared in this way are cultured in vitro under the above conditions, both the hemopoietic and fibroblastic cells die, enabling the selection and survival of only the TGFβ1-responsive cells (Gordon et al., Hum. Gene Ther., 8:1385, 1997).

Reverse Transcription-Coupled PCR Analysis (RT-PCR) For Detection of Osteoblast Specific Factor 2 (Osf2) Expression in Murine Mesenchymal and TGFβ1-Responsive Mesenchymal Progenitor Cells. Total RNA was extracted from mesenchymal and TGFβ1-responsive bone marrow cells using RNAzol reagent. Briefly, 5 µg of total RNA was treated with Superscript II Rnase H-Reverse Transcriptase (Gibco/BRL) in a 20 µl reaction volume with random hexamers. PCR amplifications were done with Gene Amp PCR system 9600 (Perkin-Elmer) and Taq DNA polymerase (Qiagen), using 2.0 µl of cDNA solution in an incubation volume of 50 µl. PCR amplifications were carried out at 94° C. for 2 minutes, followed by 30 cycles at 94° C. for 1 minute, 55° C. for 45 seconds, 72° C. for 45 seconds, and final extension of the PCR product at 72° C. for 7 minutes. Mouse Osf2 primers were chosen from sense: 5' CATATGCTTCATTCGCCTCACAA 3' (SEQ ID NO: 2); and antisense: 5' CCC ATC TGG TAC CTC TCC 3' (SEQ ID NO: 3). The mouse 18S ribosomal primer (an internal control) was purchased from Ambion, Tex. The PCR products were analyzed by loading 4 µl for Osf2 and 2 µl for 18S from 50 µl reaction volume on a 1.6% agarose gel and visualized by ethidium bromide staining.

Differentiation of TGFβ1 Responsive Cells Into Mesenchymal and Hematopoietic Phenotypes. Seven days after reconstitution with D10 medium, the cultures were supplemented with either osteoinductive agents ($10^{-8}$M dexamethasone, $2.8 \times 10^{-4}$M ascorbic acid and 10 mM β-glycerol phosphate in D10 medium), epidermal growth factor (EGF, 10 ng/ml), TGFβ1-vWF (concentration: 1 ng/2 µl DMEM (serum-free medium)), and 200 µl neutralized collagen (Gordon et al., Hum. Gene Ther., 8:1385, 1997), hematopoietic stem cell factor (c-kit ligand or rhSCF—concentration: 50 ng/ml), interleukin 3 (IL3—concentration: 10 ng/ml) or maintained in D10 without any growth factor supplement. The cells that were supplemented with SCF or IL3 were cultured on chamber slides, and stained with leukostatin stain or immunostained with CD34, CD3, or CD45 monoclonal antibodies (University Pathologists, University of Southern California School of Medicine, Los Angeles, Calif.).

Results

Isolation, Differentiation, and Morphological Distinctions Between TGFβ1-Responsive Stem Cells and Fibroblastic Mesenchymal Stem Cells. Previous studies characterized the methodologies employed to isolate a stem cell of mesodermal origin and described its potential utility in gene therapy applications. This technology involved the culture of bone marrow-derived cells on collagen matrices impregnated with a TGFβ fusion protein bearing an auxiliary collagen-binding domain, under highly selective conditions. Clear morphological distinctions between the adherent fibroblastic stem cell isolated from bone marrow stroma and operationally designated mesenchymal stem cell (MSC) (Pittinger et al., Science, 284:143, 1999; Dennis et al., J. Bone Miner. Res., 14:700, 1999), and the non-adherent blastoid precursor cells captured by TGFβ1-vWF selection and referred to as pre-mesenchymal stem cells (PMC) is shown in FIG. 1.

Figure 2:
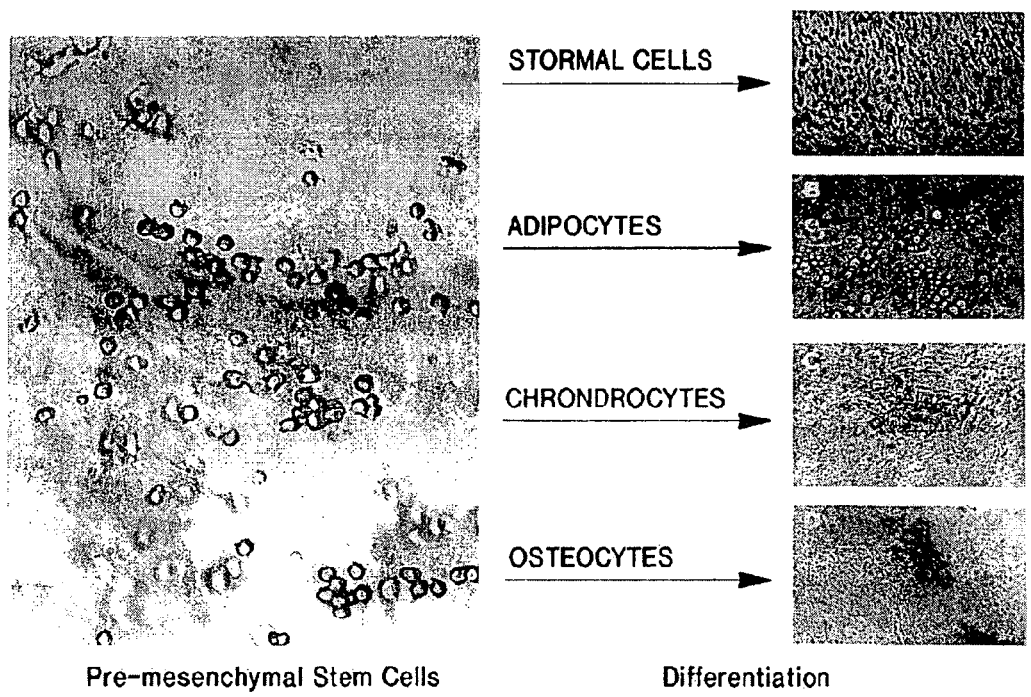
FIG. 2 shows photographs of pre-mesenchymal stem cell differentiation. TGFβ1-responsive pre-mesenchymal stem cells can be expanded in culture (left plate) and induced to differentiate into stromal cells (Panel A), adipocytes (Panel B), chondrocytes (Panel C), or osteocytes (Panel D) under growth factor-supplemented culture conditions.

Differentiation of TGFβ1-Responsive Cells Into Mesenchymal Phenotypes. The subsequent differentiation of blastoid pre-mesenchymal stem cells under defined conditions into: (i) stromal cells, (ii) adipocytes, (iii) chondrocytes, and (iv) osteocytes is shown in FIG. 2. The present study indicates that TGFβ1-responsive cell cultures maintained in D10 differentiated into stromal cells which were vimentin positive, while cell cultures supplemented with osteoinductive factors formed bone-forming colonies evidenced by calcium deposition. Additionally, supplementation with TGFβ1-induced differentiation into chondrocytes that were positive for collagen, while EGF treatment-induced differentiation into adipocytes which stained positive for sudan black (FIG. 2).

Figure 3D:
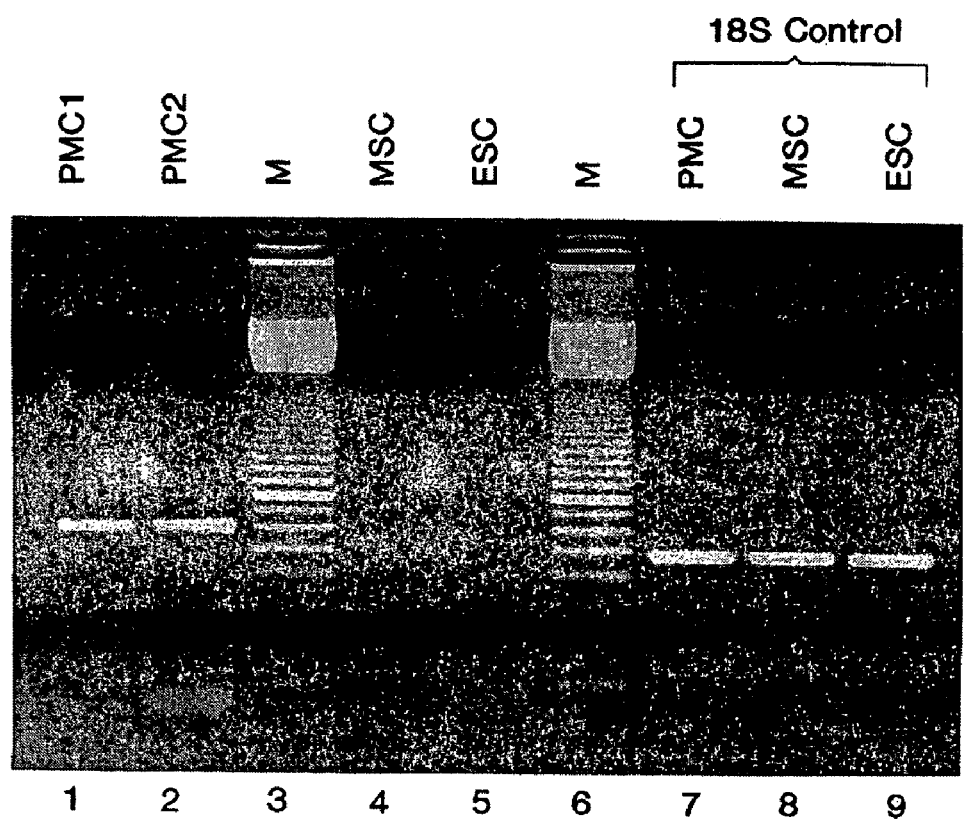
FIG. 3 shows osteoblast specific factor 2 (Osf2) is a molecular marker for TGFβ1-responsive stem cells. Panel A shows bone marrow-derived pre-mesenchymal stem cells (BM-PMSC) captured after 7 days of stringent selection on TGFβ1-vWF impregnated collagen gels. Panel B shows that the cells treated as described in Panel A exhibit a characteristic blastoid morphology. Panel C shows, by comparative reverse transcription PCR (RT-PCR), that the expression of osteoblast specific factor 2 (arrow) occurs in BM-PMSC but not in fibroblast, crude bone marrow aspirates (BM-SC), calvarial bone, whole embryo or vascular smooth muscle cells. Panel D shows the results of RT-PCR on primary cell cultures. Osteoblast specific factor 2 (Osf2) was detected in TGFβ1-selected pre-mesenchymal stem cells (PMC, Lanes 1 and 2) but not in mesenchymal stem cells (MSC) (Lane 4) or embryonic stem cells (ES, Lane 5).

Identification Of Osf2 As A Distinguishing Molecular Marker For Tgfb1-Responsive Stem Cells. Previous studies of differential gene expression in proliferative neointimal smooth muscle cells versus differentiated vascular smooth muscle cells identified osteoblast specific factor 2 (Osf2) as a molecular marker which can be used to characterize pre-mesenchymal stem cells vis-a-vis fibroblastic stromal cells (Pittinger et al., Science, 284:143, 1999). Determined by differential display PCR technology, Osf2 is dramatically up-regulated in neointimal cells which are recruited to proliferate in response to vascular injury. Osf2 (i) is present embryologically in the earliest stage mesenchymal condensations, (ii) is expressed in osteoblasts but not osteocytes, (iii) is expressed in proliferative smooth muscle precursor cells but not in differentiated SMC, and (iv) is not present in fibroblastic cells. The present study has determined, for the first time, that formulated that the Osf2 transcription factor is not osteoblast specific per se, but is mesodermal stem cell specific and, thus, may be used to identify the most embryologically primitive of the mesodermal stem cells. The "proof-of-principle" that Osf2 specifically identifies pre-mesenchymal stem cells is presented in FIG. 3, which establishes the expression of OsF2 in bone marrow-derived pre-mesenchymal stem cells (Panel C, BM-PMSC Lane 2) but not in fibroblasts (Panel C, Lane 1), crude bone marrow aspirates (Panel C, BM-SC Lane 4), calvarial bone (Panel C, Lane 5), whole embryo (Panel C, Lane 6) or mature smooth muscle cells (Panel C, Lane 7) demonstrated by RT-PCR. FIG. 3, Panel D, provides further confirmation that Osf2 is detected consistently in purified cultures of TGFβ1-responsive cells, designated pre-mesenchymal stem cells (Panel D, PMC; Lanes 1 and 2), but is not detected in mesenchymal stem cells (MSC) populations (Panel D, Lane 4) or cultures of totipotent embryonic stem (ES) cells (Panel D, Lane 5).

Figure 4:
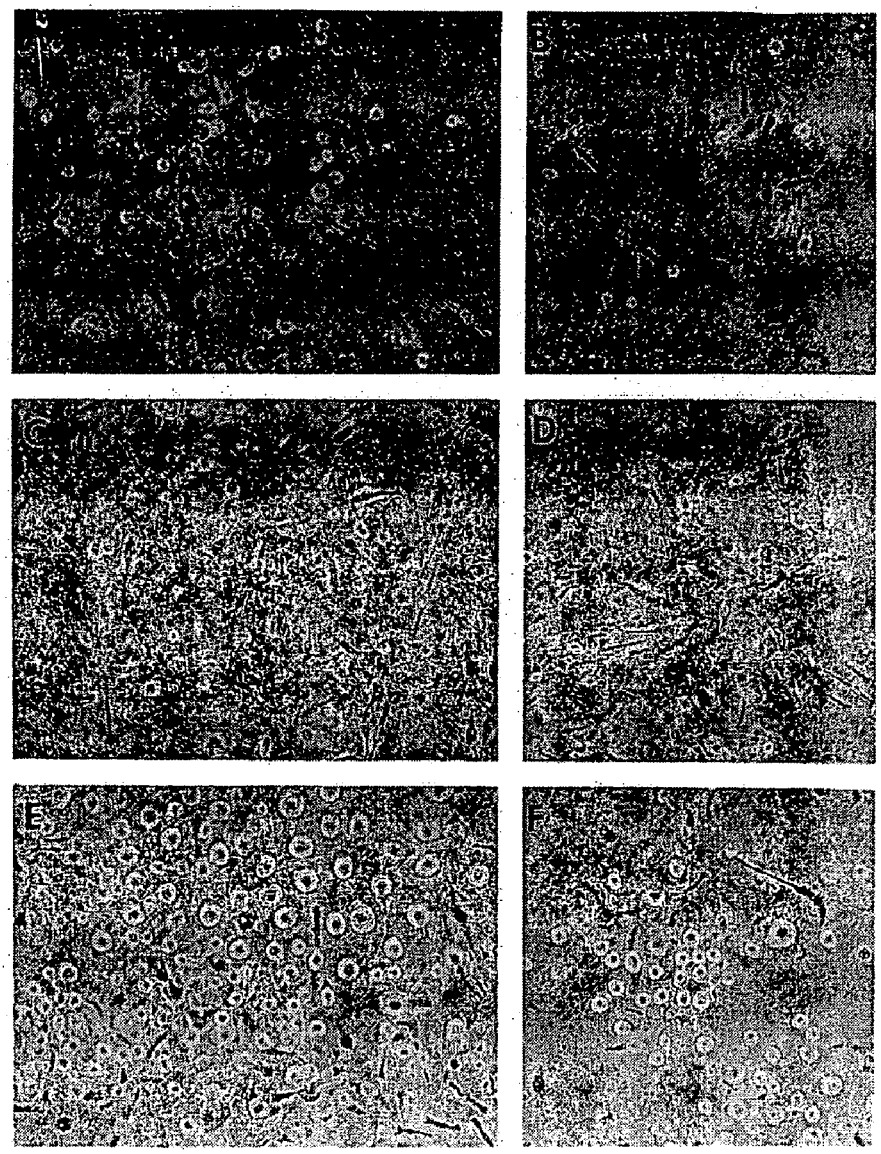
FIG. 4 shows the effects of hematopoietic growth factor treatment in TGFβ1-responsive stem cell cultures. TGFβ-selected pre-mesenchymal stem cells cultured in DMEM+10% FBS begin to proliferate (Panel A) and exhibit a limited range of differentiation: stage 1, small spherical non-adherent blasts; stage 2, filopodia extensions and a bipolar phenotype; stage 3, overt flatteing and adherence of the bipolar cells; stage 4, increase in cytoplasm and differentiation into a fibroblastic morphology (Panel B). Stem cell factor induces a significant increase in cell proliferation (Panel C) without altering the limited spectrum of overt cytodifferentiation (Panel D). In contrast, cells treated with IL3 undergo massive proliferation (Panel E) and transformation into large CFU-GEMM-like cells (Panel F).
Figure 5:
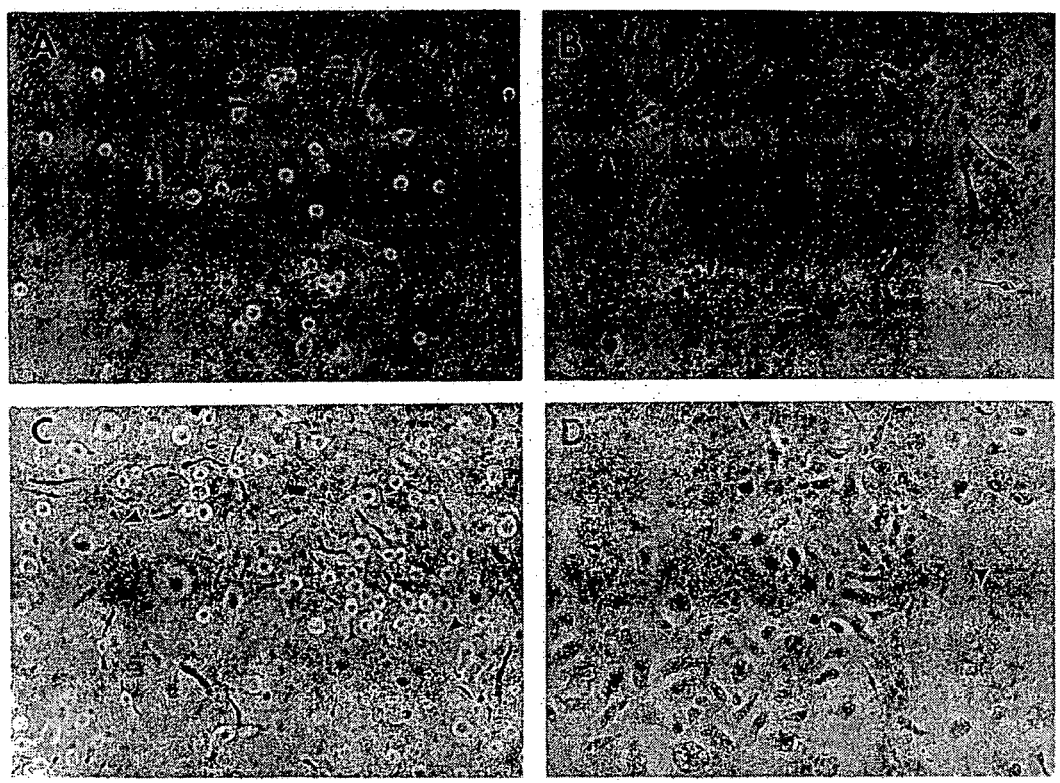
FIG. 5 shows the morphology of P4 stem cells after IL3 treatment. TGFβ1-responsive pre-mesenchymal stem cells captured on collagen gels exhibit a characteristic morphology in DMEM+10% FBS (Panel A) as shown by modified Wrights stain (Panel B). The addition of IL3 induces proliferation and the appearance of larger cells (Panel C) which exhibit a granular cytoplasm as revealed by Wrights stain (Panel D).

Responsiveness of Premesenchymal Stem Cells to Hematopoietic Growth Factors. Examination of the characteristic spherical, non-adherent morphology of the TGFβ1-responsive stem cells (FIG. 1), the observation of a host of mesenchymal phenotypes that emerged after serum reconstitution under defined conditions (FIG. 2), and the characterization of a definitive molecular marker (Osf2) for this cell type (FIG. 3), indicated that these pre-mesenchymal stem cells may indeed be primitive enough to exhibit hematopoietic differentiation potential as well. To test this hypothesis we examined the effects of two hematopoietic growth factors (i.e., SCF and IL3) on TGFβ1-responsive stem cell cultures. As shown in FIG. 4, the selected cell population began to proliferate in culture with the addition of 10% FBS. Under these conditions, a limited range of differentiation was observed (FIG. 4, Panel A and Panel B) and characterized in stages as Stage 1, small spherical blasts with high nuclear to cytoplasmic ratios; Stage 2, the appearance of thin filopodia and a bipolar phenotype; Stage 3, overt flattening of the cell body, i.e., an adherence response; and Stage 4, increased production of cytoplasm and conversion into a fibroblastic phenotype. Treatment with hematopoietic stem cell factor, SCF, induced a proliferative response (FIG. 4, Panel C and Panel D); however, the morphological phenotypes generally remained within the range of phenotypes described above (Stages 1-4). In contrast, the addition of IL3 induced a robust proliferative response (FIG. 4, Panel E and Panel F), accompanied by a marked increase in cell size, and later, by overt changes not only in the size but in the shape of the cells (stellate cells and cells with thin filopodial appendages). Examination of the morphology of the expanded cell populations in culture, as revealed by lightly staining with leukostatin, confirmed dramatically increase in the size and granularity of the cytoplasm of IL3-treated cell cultures (FIG. 5, Panel C and Panel D), compared to those treated with D10 alone (FIG. 5, Panel A and Panel B).

Figure 6:
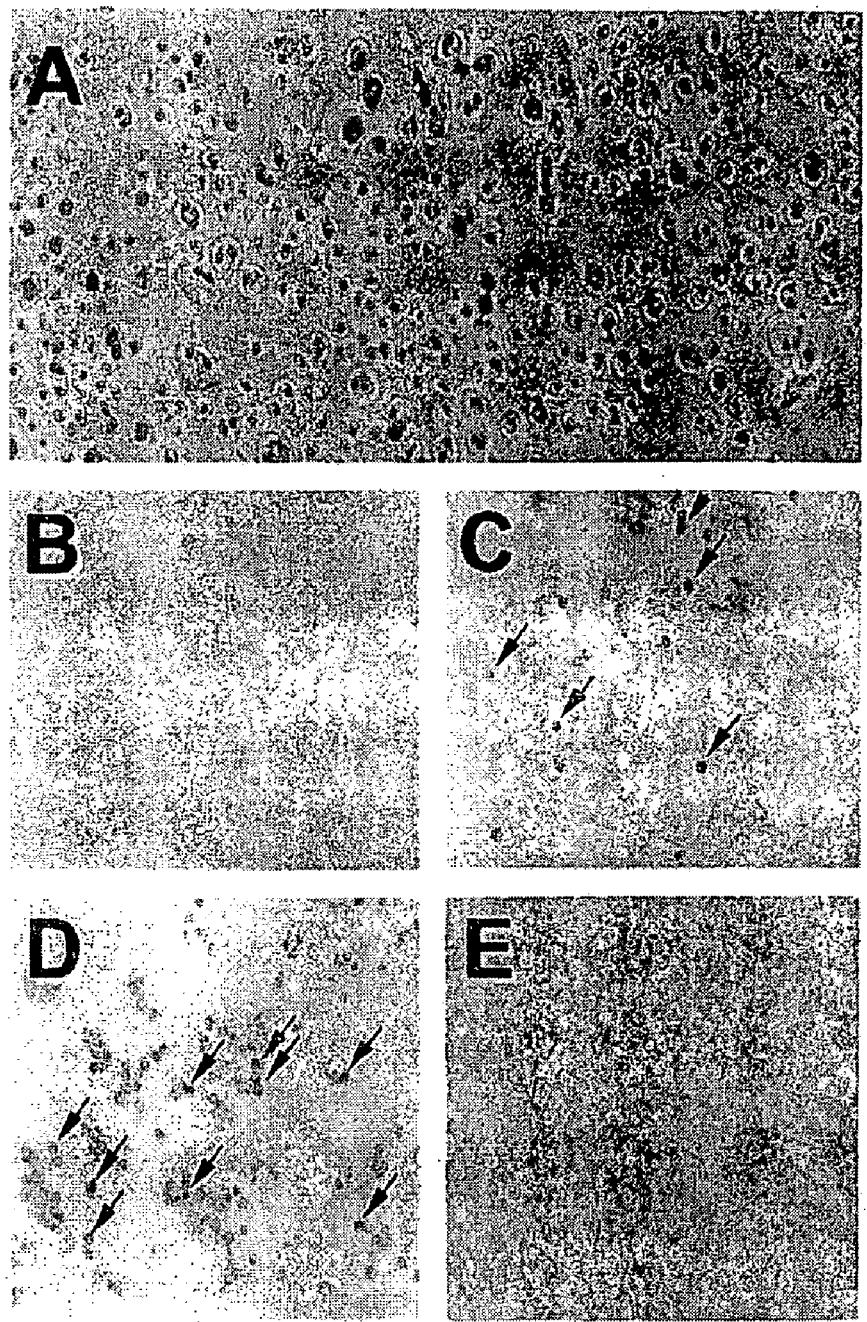
FIG. 6 shows immunostaining of P4 stem cells treated with IL3. Mature granulocytes, eosinophils, and mononuclear cells (Panel A) stained with Leukostatin stain (Panel B) CD34 negative cells (Panel C) CD45+ cells (Panel D) CD3+ cells (Panel E).

Differentiation of TGFβ1-Responsive Stem Cells Into Myeloid and Lymphoid Phenotypes in the Presence of IL3. To confirm the hematopoietic differentiation of the P4 stem cells, the IL3-treated cells were grown on chamber slides, stained with leukostatin stain, and immunostained with CD34, CD3, and CD45 monoclonal antibodies. Immunostaining of the expanded cell populations revealed that the serum-stimulated cells, as well as the stem cell factor-treated cells, were indeed CD34+. In contrast, the IL3-treated cells (FIG. 6) were largely CD34 negative (FIG. 6, Panel B), CD45+ (common leucocyte antigen; FIG. 6, Panel C), and CD3+ (T cell marker; FIG. 6, Panel D). The demonstration of a proliferative response of these TGFβ1-responsive stem cell cultures to known hematopoietic growth factors, SCF, and IL3, provide the first links to a common primitive origin of mesenchymal and hematopoietic cells. Hence, the TGFβ1-responsive stem cells are now referred to as pluripotent pre-hematopoietic, pre-mesenchymal progenitor, P4 stem cells.

Discussion

Stromal tissue is a relatively heterogeneous collection of loose and dense connective tissues distributed throughout the body. Mesenchymal, stromal, fibroblastic, reticular, reticulum, and spindle are terms often used interchangeably to describe these connective tissue cells, however, the term fibroblastic is commonly used to encompass all of these cells. Limited both by available technology and the underlying basic assumptions, successive attempts to accommodate the rapidly accumulating information relating to the cellular diversities have resulted in the construction of a number of hypothetical lineage diagrams.

One such progenitor cell type is operationally called the mesenchymal stem cell. These cells are prepared from a single cell suspension of tissues such as spleen, thymus, lymph node and bone marrow by gentle mechanical disruption, followed by passage through graded needles and sometimes a nylon mesh. Bone marrow cells are maintained in culture medium supplemented with selected lots of fetal bovine serum. Alternatively, bone marrow aspirates can be layered onto a Percoll gradient, after which a low-density fraction is collected and plated under standard culture conditions. When cells prepared in this manner are cultured in vitro under the above conditions, the majority of the hemopoietic cells die and stromal fibroblastic colonies are formed. Marrow cells cultured under these general conditions give rise to fibroblastic colonies, each derived from a single cell. In either case, non-adherent cells are removed by media change and the remaining cells grow to confluence, yielding a population of uniformly fibroblast-like cells. These adherent fibroblastic cells can be passaged under standard culture conditions and/ or can be induced to differentiate into osteogenic, chondrogenic, or adipogenic, but not hematopoietic phenotypes, under defined conditions. The majority (95-98%) of mesenchymal stem cells in these partially purified cultures are recognized by monoclonal antibodies that do not recognize osteoblasts, but do recognize other fibroblastic cells scattered throughout the dermis. Moreover, fibroblastic cells from other organs, such as the spleen and the thymus, as well as from peritoneal fluid and peripheral blood, can form bone with osteoinductive agents.

A recently developed technology uses a genetically engineered TGFβ1 fusion protein incorporating the D2 collagen-binding domain derived from coagulation von Willebrand's factor (vWF) (Tuan et al., Conn. Tiss. Res., 34:1, 1996). These collagen-targeted TGFβ-vWF fusion proteins are useful in the capture of the TGFβ1-responsive progenitor cells, as non-targeted TGFβ1 proteins lacking the auxiliary collagen binding domain do not support the survival of the progenitor cells, presumably due to the short half-life of the soluble growth factor. These TGFβ1-responsive progenitor cells have been shown: (i) to differentiate into bone-forming and stromal colonies, (ii) to be amenable to retroviral-mediated transduction for production of recombinant proteins, e.g., clotting factor IX, and (3) to be successfully transplanted into immunocompetent mice with subsequent in vivo recovery of the transferred gene product. Hence, the capture and expansion of mesenchymal progenitor cells on TGFβ1-vWF-impregnated collagen matrices could have extensive applications in gene therapy, as well as wound healing.

The present study provides a molecular marker for the identification of TGFβ1-responsive progenitor cells. Cells identified in this manner, designated as pluripotent pre-mesenchymal, pre-hematopoietic precursor cells (P4 stem cells), provide a unique class of stem cells possessing multilineage differentiation potential. The P4 stem cells described herein can be readily distinguished from fibroblastic stromal cells by a number of definitive morphological and physiological criteria. First, the P4 stem cells are uniformly small, spherical, and blastoid and are clearly non-adherent upon their initial isolation from bone marrow aspirates, whereas the fibroblastic stromal cell population is both defined and isolated on the basis of adherence to cell culture plates. Upon reconstitution of the serum factors, P4 stem cells proliferate into colony forming units, which exhibit a very limited range of phenotypic variation in culture, yet can be induced to differentiate into osteogenic precursors under defined conditions. While stromal fibroblasts and dermal fibroblasts exhibit considerable phenotypic plasticity, including fibrogenic, osteogenic, chondrogenic, and adipogenic differentiation, these cells remain morphologically fibroblastic and never assume the spherical blastoid morphology of the P4 stem cells. Moreover, the P4 stem cells identified in the present study express a definitive molecular marker, Osf2, that marks the most primitive mesenchymal condensations in the early embryo (Ducy et al., Cell, 8:747, 1997), but is not expressed in appreciable amounts in either crude bone marrow aspirates, adherent mesenchymal stem cells, or totipotent embryonic stem cells (See, for example, FIG. 3). Third, the P4 stem cells respond uniformly to defined hematopoietic growth factors, such as IL3, with a marked increase in cell proliferation and differentiation into myeloid and lymphoid phenotypes, as evidenced by positive staining for CD45 and CD3, respectively. These data indicate that a primitive pre-mesenchymal, pre-hematopoietic stem cell exists in the post-natal murine bone marrow, and can be isolated under stringent conditions, expanded in number for large-scale production, and induced to differentiate along either mesengenic or hematopoietic pathways.

Unlike the hematopoietic lineage, where the identity, differentiation and stages of cell lineage are relatively well defined, the terminology and lineage of the so-called "mesenchymal stem cell" remains operationally, rather than biochemically or immunohistochemically characterized. While the functional isolation of hematopoietic stem cells by utilizing selective growth conditions has been reported, the isolation of mesenchymal precursor cells by selective physiological conditions, wherein cytocidal conditions are combined with a long-acting growth/survival factor embedded in a supportive collagen matrix, represents a unique purification strategy. The expression of the Osf2 transcription factor can be used to identify and characterize the fractionated cell populations.

A number of embodiments of the invention have been described. Nevertheless, it will be understood that various modifications may be made without departing from the spirit and scope of the invention. Accordingly, other embodiments are within the scope of the following claims.

What is claimed is:

1. A method for identifying if a pre-mesenchymal, pre-hematopoietic stem cell is present in a population of cells, comprising:
 (a) obtaining a population of cells from the bone marrow of an animal;
 (b) culturing in a collagen gel the cells of (a) in medium comprising 1.0% or less serum in vitro for at least seven days with a polypeptide comprising a fusion polypeptide, wherein the fusion polypeptide comprises a collagen-binding domain and TGF-β1 or active fragment of TGF-β1;
 (c) culturing the TGF-β1 responsive cells of (b); and
 (d) detecting expression of osteoblast specific factor 2 (Osf2) in said TGF-β1 responsive cells; thereby identifying a cell that expresses Osf2 as a pre-mesenchymal, pre-hematopoietic stem cell.

2. The method of claim 1, wherein the collagen-binding domain is a collagen-binding domain of von Willebrand factor.

3. The method of claim 2, wherein the collagen-binding domain of von Willebrand factor comprises the decapeptide WREPSFMALS (SEQ ID NO:1).

4. The method of claim 1, wherein step (d) comprises detecting Osf2 RNA.

5. The method of claim 1, wherein step (d) comprises detecting the Osf2 polypeptide.

6. The method of claim 1, wherein the animal is a mammal.

7. The method of claim 6, wherein the mammal is selected from the group consisting of primate, swine, porcine, feline, canine, equine, murine, cervine, caprine, lupine, leporidine, and bovine.

8. The method of claim 7, wherein the primate is a human.

* * * * *

SEQUENCE LISTING

<160> NUMBER OF SEQ ID NOS: 3

<210> SEQ ID NO 1
<211> LENGTH: 10
<212> TYPE: PRT
<213> ORGANISM: Homosapien

<400> SEQUENCE: 1

Trp Arg Glu Pro Ser Phe Met Ala Leu Ser
 1               5                  10

<210> SEQ ID NO 2
<211> LENGTH: 23
<212> TYPE: DNA
<213> ORGANISM: Homosapien

<400> SEQUENCE: 2
catatgcttc attcgcctca caa                                          23

<210> SEQ ID NO 3
<211> LENGTH: 18
<212> TYPE: DNA
<213> ORGANISM: Homosapien

<400> SEQUENCE: 3
cccatctggt acctctcc                                                18